United States Patent [19]

Makino et al.

[11] Patent Number: 5,026,560
[45] Date of Patent: Jun. 25, 1991

[54] SPHERICAL GRANULES HAVING CORE AND THEIR PRODUCTION

[75] Inventors: Tadashi Makino; Tetsuro Tabata, both of Osaka; Shin-ichiro Hirai, Kyoto, all of Japan

[73] Assignee: Takeda Chemical Industries, Ltd., Osaka, Japan

[21] Appl. No.: 143,957

[22] Filed: Jan. 14, 1988

[30] Foreign Application Priority Data

Jan. 29, 1987 [JP] Japan ................................. 62-19178

[51] Int. Cl.⁵ .......................... A61K 9/16; A61K 9/36; A61K 9/62

[52] U.S. Cl. ..................................... 424/494; 424/458; 424/461; 424/468; 424/480; 424/489; 424/490; 424/479; 424/493; 424/497; 514/925

[58] Field of Search ..................... 424/490, 494, 480

[56] References Cited

U.S. PATENT DOCUMENTS

| | | | |
|---|---|---|---|
| 3,477,864 | 11/1969 | Tuji | 424/497 X |
| 4,226,849 | 10/1980 | Schor | 424/469 |
| 4,695,591 | 9/1987 | Hanna et al. | 424/480 X |
| 4,758,437 | 7/1988 | Sonobe et al. | 424/471 |
| 4,786,505 | 11/1988 | Lovgren et al. | 424/468 |

FOREIGN PATENT DOCUMENTS

| | | |
|---|---|---|
| 0159891 | 10/1985 | European Pat. Off. . |
| 0200902 | 11/1986 | European Pat. Off. . |
| 0244380 | 11/1987 | European Pat. Off. . |
| 2134523 | 8/1984 | United Kingdom . |

OTHER PUBLICATIONS

Drug Development and Industrial Pharmacy, 11(8), 1523-1541 (1985).

*Primary Examiner*—Thurman K. Page
*Assistant Examiner*—James M. Spear
*Attorney, Agent, or Firm*—Wegner, Cantor, Mueller & Player

[57] ABSTRACT

The spherical granules having a core coated with spraying powder containing a drug and low substituted hydroxypropylcellulose, because of their excellent hardness, can be coated further evenly, (e.g. sustained release coating, gastric coating, enteric coating), and at the time the granules are excellent in disintegration.

30 Claims, No Drawings

SPHERICAL GRANULES HAVING CORE AND THEIR PRODUCTION

This invention relates to spherical granules having a core excellent in hardness and disintegration, and to their production.

Recently many studies have been made on drug delivery systems; especially as the dosage form for oral administration, granules coated with various coating agents, i.e. so-called coating granules have been used increasingly frequently, and the granules as they are or capsules produced by filling the granules in capsules have been developed.

As reasons for this fact may be mentioned that granules, as compared with tablets biopharmaceutically, reduce individual variations in gastric emptying rate, absorption, etc. and little affected by food (intake).

For production of spherical granules, the method wherein after granulation by extrusion the granules are made spherical with a marumerizer is most commonly used, but the granules thus produced are mostly not perfect spheres and the granule size distribution is wide; therefore it is said that uniform coating is so difficult that pharmaceutical preparations for precisely controlled release are difficult to be obtained.

On the other hand, recently a centrifugal fluidized-bed coating-granulator (sometimes abbreviated as CF granulator hereinafter) has been developed, and a method to make the granules spherical with this granulator has been tried.

In this method the surface of a spherical seed core or core is coated, while being sprayed with water or a solution containing a binder, with a spraying powder containing a drug, and thus spherical granules of high perfect sphere content and narrow granule size distribution are obtained. [See Drug Development and Industrial Pharmacy, 11(8), 1523-1541 (1985).]

To produce pharmaceutical preparations for controlled release the surface of the resulting spherical granules is coated with wax or polymer for the purpose of control of release of the drug. The coating is performed generally by fluidized-bed coating.

In the initial phase of the process of the fluidized-bed coating, there occur frequently troubles such as breaking and scraping of the spherical granules. These troubles not only damage the drug release control function but also affect greatly the yield in production of granules: thus a method for production of spherical granules excellent in hardness and disintegration has been desired Under these circumstances, the inventors investigated the method for production of spherical granules excellent in hardness and disintegration by using the CF granulator, and have completed this invention.

This invention relates to
(1) spherical granules having a core coated with spraying powder containing a drug and low substituted hydroxypropylcellulose, and to
(2) a method for producing spherical granules having a core characterized in that seed cores are coated, while being sprayed with an aqueous binder, with spraying powder containing a drug and low substituted hydroxypropylcellulose.

The content of the hydroxypropoxyl group in the low substituted hydroxypropylcellulose (sometimes abbreviated as L-HPC hereinafter) used in this invention is generally about 4-20%, preferably 5.0-16.0%, more preferably 10.0-13.0%. The mean particle size of the L-HPC may generally be not more than 200 μm in diameter, preferably not more than 100 μm, more preferably not more than 30μm.

The drugs are not particularly defined as far as they can be used in the form of granules, including drugs for the central nervous system such as diazepam, idebenone, aspirin, ibuprofen, paracetamol, naproxen, piroxicam, diclofenac, indomethacin, sulindac, lorazepam, nitrazepam, phenytoin, acetaminophen, ethenzamide, and ketoprofen; drugs for the circulatory system such as molsidomine, vinpocetine, propranolol, methyldopa, dipyridamole, furosemide, triamterene, nifedipine, atenolol, spironolactone, metoprolol, pindolol, captopril, and isosorbide nitrate, drugs for the respiratory system such as amlexanox, dextromethorphan, theophylline, pseudoephedrine, salbutamol, and guaifenesin; drugs for the digestive system such as benzimidazoles described below, cimetidine, ranitidine, pancreatin, and 5-aminosalicylic acid; antibiotics and chemotherapeutic agents such as cephalexin, cefaclor, cefradine, amoxicillin, pivampicillin, bacampicillin, dicloxacillin, erythromycin, erythromycin stearate, lincomycin, doxycycline, trimethoprim, and sulfamethoxazole; drugs for metabolic system such as serrapeptase, glibenclamide, and potassium chloride; and vitamin drugs such as vitamin $B_1$, vitamin $B_2$, vitamin $B_6$, vitamin C, and fursultiamine.

The said benzimidazoles include those described in U.S. Pat. No. 4045563, U.S. Pat. No. 4255431, European Patent Publication No. 45200 U.S. Pat. No. 4472409, European Patent Publication No. 5129, British Patent Publication No. 2134523, European Patent Publication No. 174726, European Patent Publication No. 175464, and European Patent Publication No. 208452 etc.

The benzimdazoles having antiulcer activity, which are described in the above laid-open patent specifications, for instance are represented by the formula

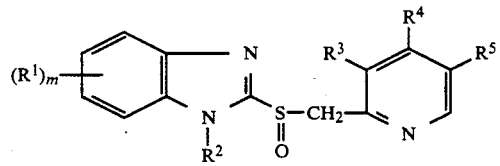

wherein
$R^1$ is hydrogen, alkyl, halogen, cyano, carboxy, carboalkoxy, carboalkoxyalkyl, carbamoyl, carbamoylalkyl, hydroxy, alkoxy, hydroxyalkyl, trifluoromethyl, acyl, carbamoyloxy, nitro, acyloxy, aryl, aryloxy, alkylthio or alkylsulfinyl,
$R^2$ is hydrogen, alkyl, acyl, carboalkoxy, carbamoyl, alkylcarbamoyl, dialkylcarbamoyl, alkylcarbonylmethyl, alkoxycarbonylmethyl or alkylsulfonyl,
$R^3$ and $R^5$ are the same or different and each is hydrogen, alkyl, alkoxy or alkoxyalkoxy,
$R^4$ is hydrogen, alkyl, alkoxy which may optionally be fluorinated, or alkoxyalkoxy, and m is an integer of 0 through 4.

The compounds of the formula (I) can be produced by the methods described in the above-cited laid-open patent specifications or modifications thereof.

In the following, brief mention is made of the substituents in those compounds which have the formula (I) and are already known.

Referring to $R^1$ in the above formula, $C_{1-7}$ alkyls may be mentioned as the alkyl represented by $R^1$; $C_{1-4}$ alkoxys as the alkoxy moiety of the carboalkoxy; $C_{1-4}$ alkoxys as the alkoxy moiety of the carboalkoxyalkyl and $C_{1-4}$ alkyls as the alkyl moiety; $C_{1-4}$ alkyls as the alkyl moiety of the carbamoylalkyl: $C_{1-5}$ alkoxys as the alkoxy; $C_{1-7}$ alkyls as the alkyl moiety of the hydroxyalkyl; $C_{1-4}$ alkanoyls as the acyl; phenyl as the aryl; phenyl as the aryl moiety of the aryloxy; $C_{1-6}$ alkyls as the alkyl moiety of the alkylthio; and $C_{1-6}$ alkyls as the alkyl moiety of the alkylsulfinyl.

Referring to $R^2$, $C_{1-5}$ alkyls may be mentioned as the alkyl represented by $R^2$; $C_{1-4}$ alkanoyls as the acyl; $C_{1-4}$ alkoxys as the alkoxy moiety of the carboalkoxy; $C_{1-4}$ alkyls as the alkyl moiety of the alkylcarbamoyl ; $C_{1-4}$ alkyls as each of the alkyl moieties of the dialkylcarbamoyl: $C_{1-4}$ alkyls as the alkyl moiety of the alkylcarbonylmethyl; $C_{1-4}$ alkoxys as the alkoxy moiety of the alkoxycarbonylmethyl; and $C_{1-4}$ alkyls as the alkyl moiety of the alkylsulfonyl.

Referring to $R^3$, $R^4$ and $R^5$, $C_{1-4}$ alkyls may be mentioned as the alkyl represented by any of them; $C_{1-8}$ alkoxys as the alkoxy; and $C_{1-4}$ alkoxys as each of the alkoxy moieties of the alkoxyalkoxy.

Referring to $R^4$, $C_{1-8}$ alkoxys may be mentioned as the alkoxy, which may optionally be fluorinated.

More specifically, they include 2-[[3-methyl-4(2,2,2-trifluoroethoxy)-2-pyridyl]methylsulfinyl]benzimidazole, and 5-methoxy-2-[(4-methoxy-3,5-dimethyl-2pyridyl)methylsulfinyl]benzimidazole etc.

The said seed cores include Nonpareil produced by coating sucrose (75 weight parts) with corn starch (25 weight parts) according to the per se known method, and spherical seed cores using crystalline cellulose. The drug may be used as the seed core. The particle size of the said seed cores is generally 14-80 mesh.

The said aqueous binder includes water, ethanol (concentration: preferably 50% (v/v) or less), and solutions of binders in water or in ethanol; the concentration of the said solutions is generally 0.1-80% (w/v), preferably 0.5-70% (w/v). The said binders include sucrose, hydroxypropylcellulose, hydroxypropylmethylcellulose, methylcellulose, polyvinylpyrrolidone, pullulan, and gum arabic, which may be used alone or in combination.

The spraying powder containing the drug and L-HPC in this invention may be combined further with powdery additives. The said additives include excipients (e.g. lactose, corn starch, sucrose, crystalline cellulose, light anhydrous silicic acid), binders (e.g.c -starch, methylcellulose, carboxymethylcellulose, hydroxypropylcellulose, hydroxypropylmethylcellulose, polyvinylpyrrolidone, pullulan, dextrin, gum arabic), disintegrators (e.g. calcium carboxymethylcellulose, starch), stabilizers (e.g. magnesium carbonate, calcium carbonate, L-cystein), and coloring agents (e.g. talc, iron sesquioxide, tar colors).

The said spraying powder in this invention are obtained by mixing uniformly the drug, L-HPC, and the additives described above, and the particle size is generally not more than about 100 μm, preferably not more than about 50 μm.

The combination ratio of L-HPC to the spraying powder is preferably about 5-90% (w/w), more preferably about 10 -60% (w/w).

The combination ratio of the drug to the spraying powder depends upon the kind and the dose of the drug, being about 2-70% (w/w), preferably about 5-50% (w/w).

In the following the method for production of spherical granules having a core of this invention is described in detail. The conditions under which seed cores are coated with spraying powder while being sprayed with an aqueous binder are: the ratio of the aqueous binder to the spraying powder of about 1:1-1:2 is adequate; the production temperature need not be controlled; being generally room temperature (1-30° C.). Spherical granules having a core of even size are obtained by sieving after drying. For example, 12-32 mesh round sieves are used, and the granules which pass through the 12 mesh sieve but do not pass through the 32 mesh sieve are selected.

The spherical granules having a core thus obtained may be coated according to the per se known method for the purpose of taste masking, enteric coating, gastric coating, or prolongation, and/or filled n capsules according to the per se known method.

The said coating agents include hydroxypropylmethylcellulose, ethylcellulose, hydroxymethylcellulose, hydroxypropylcellulose, polyoxyethyleneglycol, Tween 80, pluronic F 68, castor oil, cellulose acetate phthalate, hydroxypropylmethylcellulose phthalate, hydroxymethylcellulose acetate succinate, Eudragit (Röhm Pharma Co., West Germany, acrylate copolymer, amionic in character), carboxymethylethylcellulose, polyvinylacetaldiethylaminoacetate, waxes, and pigments such as talc, titanium oxide, ferric oxide.

The spherical granules having a core of this invention, because of their excellent hardness, can be further coated evenly (e.g. sustained release coating, gastric coating, enteric coating), and at the same time the granules are excellent in disintegration.

In the following, this invention is illustrated in detail with working examples and experimental examples, which however should not limit this invention.

EXAMPLE

Nonpareils (20-28 mesh), 2250 g, were the CF granulator (CF-360, Freund Industrial Co., Ltd., Japan), and coated, while being sprayed with 2000 ml of hydroxypropylcellulose solution (3% (w/v)) at 25 ml/min, first with the spraying powder 1 and then the spraying powder 2, both of which had been prepared by mixing the ingredients listed below, at the rate of 45 g/min at room temperature with a rotor rotating at 200 rpm, dried under reduced pressure at 40° C. for 16 hours, and sieved through round sieves, to give spherical granules having a core of 12-32 mesh.

[spraying powder 1]

compound A* :450 g
magnesium carbonate : 450 g
sucrose : 450 g
corn starch : 450 g
L-HPC : 450 g
(degree of substitution with hydroxypropxyl group: 10.0-13.0% (w/w), mean particle size: not more than 30 μm. The particles of the same degree of substitution and particle size were used hereinafter.)
* Compound A: 2-[[3-methyl-4-(2,2,2-trifluoroethoxy)-2-pyridyl]methylsulfinyl]benzimidazole [spraying powder 2]
sucrose : 420 g
corn starch : 360 g
L-HPC : 360 g

EXAMPLE 2

The granules obtained in Example 1, 3800 g, were brought into the fluidized-bed coator (Okawara Co., Japan), subjected to enteric coating by spraying the enteric coating film solution described below at the rate of 50 ml/min under the controlled conditions of inlet air at 50° C. and material temperature at 40° C., to give enteric coated spherical granules having core The said granules were filled into No.2 hard capsules with a capsule filling machine (Parke-Davis Co., USA), to give capsules

| [Enteric coating film solution] | |
| --- | --- |
| Eudragit L30D-55 | 628 g |
| talc | 192 g |
| polyethyleneglycol 6000 | 64 g |
| titanium oxide | 64 g |
| Tween 80 | 32 g |
| water | 4400 ml |
| [composition of the capsules] | |
| enteric coated granules | 240 mg |
| No. 2 hard capsule | 65 mg |
| | 305 mg (per capsule) |

EXAMPLE 3

Nonpareils (20-28 mesh), 85 g, were brought into mini CF granulator(Freund Co.), and coated, while being sprayed with water (50 ml) at 2.5 ml/min, with the spraying powder described below at the rate of 5 g/min with a rotor rotating at 400 rpm, dried under reduced pressure at 40° C. for 16 hours and sieved through round sieves, to give spherical granules having acore of 12-32 mesh.

[spraying powder]

pancreatin : 20 g
sucrose : 40 g
corn starch : 20 g
L-HPC : 20 g

EXAMPLE 4

Nonpareils (24-32 mesh), 2 kg, were brought into a CF granulator (CF-360, Freund Co.), and coated, while being sprayed with 1% (w/v) hydroxypropylcellulose solution (1000 ml) at 20 ml/min, with the the spraying powder described below at the rate of 40 g/min with a rotor rotating at 200 rpm, dried under reduced pressure at 40° C. for 16 hours, and sieved through round sieves, to give spherical granules having a on of 12-32 mesh.

[spraying powder]

serrapeptase : 50 g
sucrose : 1350 g
corn starch : 200 g
L-HPC : 400 g

Then the granules thus obtained, 300 g, were brought into the fluidized-bed coator (Okawara Co., Japan), subjected to enteric coating by spraying the enteric coating film solution described below at the rate of 50 ml/min under the controlled conditions of inlet air at 50° C. and material temperature at 40° C., to give enteric coated spherical granules having a core.

[Enteric coating film solution]

hydroxypropylmethylcellulose phthalate a 1000 g
castor oil : 100 g
talc : 20 g
acetone : 10000 ml

EXAMPLE 5

Nonpareils (24-32 mesh), 85 g, were brought into a mini CF granulator (Freund Co.), and coated, while being sprayed with 50% (w/v) solution of sucrose (50 ml) at 5 ml/min, with the spraying powder described below at the rate of 10 g/min with a rotor rotating at 400 rpm, dried under reduced pressure at 40° C. for 16 hours, and sieved through round sieves, to give spherical granules having a core of 12-32 mesh.

[spraying powder]

molsidomine : 5 g
sucrose : 55 g
corn starch : 20 g
L-HPC : 20 g

EXAMPLE 6

Nonpareils (24-32 mesh), 85 g, were brought into a mini CF granulator(Freund Co.), and coated, while being sprayed with 1% (w/v) solution of hydroxypropylmethylcellulose (50 ml) at 2.5 ml/min, with the spraying powder described below at the rate of 5 g/min with a rotor rotating at 400 rpm, dried under reduced pressure at 40° C. for 16 hours, and sieved through round sieves, to give spherical granules having a core of 12-32 mesh.

[spraying powder]

idebenone : 20 g
sucrose : 20 g
corn starch : 25 g
L-HPC : 35 g

EXAMPLE 7

Spherical seed cores of crystalline cellulose (20-32 mesh), 85 g, were brought into a mini CF granulator (Freund Co.), and coated, while being sprayed with 1% (w/v) solution of pullulan (50 ml) at 2.5 ml/min, with the the spraying powder described below at the rate of 5 g/min with a rotor rotating at 300 rpm, dried under reduced pressure at 40° C. for 16 hours, and sieved through round sieves, to give spherical granules having a core of 12-32 mesh.

[spraying powder]

amlexanox : 25 g
hydroxypropylmethylcellulose : 20 g
corn starch : 25 g
L-HPC : 30 g

EXAMPLE 8

Crystals of vitamin C (42-60 mesh), 80 g, were brought into a mini CF granulator(Freund Co.), and coated, while being sprayed with 2% (w/v) solution of hydroxypropylcellulose (60 ml) at 2.5 ml/min, with the spraying powder described below at the rate of 5 g/min with a rotor rotating at 400 rpm, dried under reduced pressure at 40° C. for 16 hours, and sieved through round sieves, to give spherical granules having a core of 12-32 mesh.

[spraying powder]

cefaclor : 50 g
sucrose : 20 g
corn starch : 10 g

L-HPC : 40 g

EXAMPLE 9

Crystals of sucrose (42–60 mesh), 85 g, were brought into a mini CF granulator(Freund Co.), and coated, while being sprayed with water (50 ml) at 2.5 ml/min, with the the spraying powder described below at the rate of 5 g/min with a rotor rotating at 400 rpm, dried under reduced pressure at 40° C. for 16 hours, and sieved through round sieves, to give spherical granules having a core of 12–32 mesh.

[spraying powder]

fursultiamine : 5 g
sucrose : 35 g
corn starch : 30 g
L-HPC : 30 g

EXAMPLE 10

Nonpareils (20–28 mesh), 1650 g, were brought into the CF granulator (CF-360, Freund Co.), and coated, while being sprayed with 1050 ml of hydroxypropylcellulose solution (2% (w/v)) at 30 ml/min, first with the spraying powder 1 and then the spraying powder 2, both of which had been prepared by mixing the ingredients listed below, at the rate of 60 g/min at room temperature with a rotor rotating at 250 rpm, dried under reduced pressure at 40° C. for 16 hours, and sieved through round sieves, to give spherical granules having a core of 14–32 mesh.

[spraying powder 1]

compound A*: 450 g
magnesium carbonate : 336 g
sucrose : 297 g
corn starch : 300 g
L-HPC : 354 g

* Compound A: 2-[[3-methyl-4-(2,2,2-trifluoroethoxy)2-pyridyl]methylsulfinyl]benzimidazole

[spraying powder 2]

sucrose : 300 g
corn starch : 246 g
L L-HPC : 354 g

EXAMPLE 11

The granules obtained in Example 10, 3800 g, Were brought into the fluidized-bed coator (Okawara Co.; Japan), subjected to enteric coating by spraying the enteric coating film solution described below at the rate of 50 ml/min under the controlled conditions of inlet air at 65° C. and material temperature at 40° C., to give enteric coated spherical granules having core. To the said granules were added talc and light anhydrous silicic acid, then filled into No. 1 hard capsules with a capsule filling machine (Parke-Davis Co., USA) to give capsules.

[Enteric coating film solution ]

Eudragit L30D-55: 2018 g (solid: 605 g)
talc: 1832 g
polyethyleneglycol 6000 : 60 g
titanium oxide: 60 g
Tween 80 : 27 g
water : 4230 ml

[composition of the capsules]

| | |
|---|---|
| enteric coated granules | 348.8 mg |
| ⎡ compound A | 30.0 mg |
|   magnesium carbonate | 22.4 mg |
|   Nonpareils | 110.0 mg |
|   sucrose | 39.8 mg |
|   corn starch | 36.4 mg |
|   L-HPC | 40.0 mg |
|   hydroxypropylcellulose | 1.4 mg |
|   Eudragit L 30D-55 | 44.6 mg |
|   talc | 13.4 mg |
|   polyethyleneglycol 6000 | 4.4 mg |
|   titanium oxide | 4.4 mg |
| ⎣ Tween 80 | 2.0 mg |
| talc | 0.6 mg |
| light anhydrous silicic acid | 0.6 mg |
| No. 1 hard capsule | 79.0 mg |
| | 429.0 mg (per capsule) |

EXPERIMENTAL EXAMPLE 1

In the method of Example 3 , coating was performed with the spraying powder containing the ingredients listed in Table 1 in place of L-HPC to produce spherical granules having core. The said granules thus obtained (12–32 mesh), 5 g, were brought into a 50 ml stainless steel cylinder (50 ml, 32 mm in diameter), shaken in a mill (Spex Co., .Spexmill) for 30 minutes, and sieved through a 32 mesh round sieve. The residual amount on the sieve was measured to calculate friability for evaluation of hardness of the granules. In addition, disintegration time was also determined according to the method described in the 11th Japanese Pharmacopoeia. Table 1
Hardness and Disintegration Time of the Granules

| | | Hardness (%) | Disintegration time |
|---|---|---|---|
| This invention | L-HPC | 98 | 1 min |
| Controls | crystalline cellulose | 87 | 2 min |
| | α-starch | 89 | not less than 30 min |
| | hydroxypropylcellulose | 90 | 10 min |
| | hydroxypropylmethyl-cellulose | 89 | 6 min |
| | polyvinylpyrrolidone | 85 | 4 min |
| | pullulan | 88 | 1.5 min |
| | methylcellulose | 84 | 2 min |
| | dextrin | 85 | 1 min |
| | gum arabic | 82 | 1 min |
| | carboxymethylcellulose | 86 | 2 min |

These results show evidently that the spherical granules having a ogre of this invention are excellent in hardness and disintegration.

What is claimed is:

1. Spherical granules having a core coated with a binder and spraying powder containing a drug and low substituted hydroxypropylcellulose having a mean particle diameter not more than 200 μm, wherein the low substituted hydroxypropylcellulose contains 4 to 20% of a hydroxypropoxyl group.

2. The spehrical granules having a core according to claim 1, wherein the drug is a drug for the digestive system.

3. The spherical granules having a core according to claim 2, wherein the drug for the digestive system is a benzimidazole compound having antiulcer activity, cimetidine, ranitidine, pancreatin or 5-aminosalicylic acid.

4. The spherical granules having a core according to claim 3, wherein the benzimdazole compound is represented by the formula

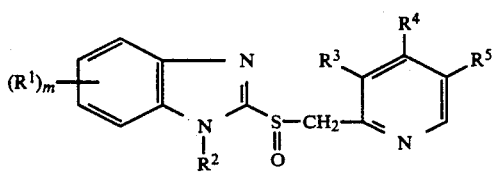

wherein
 $R^1$ is hydrogen, alkyl, halogen, cyano, carboxy, carboalkoxy, carboalkoxyalkyl, carbamoyl, carbamoylalkyl, hydroxy, alkoxy, hydroxyalkyl, trifuluoromethyl, acyl, carbamoyloxy, nitro, acyloxy, aryl, aryloxy, alkylthio or alkylsulfinyl,
 $R^2$ is hydrogen, alkyl, acyl, carboalkoxy, carbamoyl, alkylcarbamoyl, dialkylcarbamoyl, alkylcarbonylmethyl, alkoxycarbonylmethyl or alkylsulfon
 $R^3$ and $R^5$ are the same or different and each is hydrogen, alkyl, alkoxy or alkoxyalkoxy,
 $R^4$ is hydrogen, alkyl, alkoxy which may optionally be fluorinated, or alkoxyalkoxy, and m is an integer of 0 through 4.

5. The spherical granules having a core according to claim 3, wherein the benzimidazole compound is 2-[[3-methyl-4-(2,2,2-trifluoroethoxy)-2pyridyl]methylsulfinyl]benzimidazole or 5-methoxy-2-[(4-methoxy-3,5-dimethyl-2-pyridyl)-methylsulfinyl]benzimidazole.

6. The spherical granules having a core according to claim 1, wherein the content is 5.0 to 16.0%.

7. The spherical granules having a core according to claim 1, wherein the content is 10.0 to 13.0%.

8. The spherical granules having a core according to claim 1, wherein the mean particle diameter is not more then 100 μm.

9. The spherical granules having a core according to claim 1, wherein the mean particle diameter is not more than 30 μm.

10. The spherical granules having a core according to claim 1, wherein the granules pass through 12 mesh sieve but do not pass through 32 mesh sieve.

11. The spherical granules having a core according to claim 1, wherein the granules are enteric-coated.

12. A method for producing spherical granules having acore characterized in that seed cores are coated, while being sprayed with an aqueous binder, with spraying powder containing a drug and low substituted hydroxypropylcellulose having a means particle diameter not more than 200 μm, wherein the low substituted hydroxypropylcellulose contains 4 to 20% of a hydroxypropoxyl group.

13. The method according to claim 12, wherein the seed cores are nonpareils produced by coating 75 weight parts of sucrose with 25 weight parts of corn starch

14. The method according to claim 12, wherein the seed cores are made with crystalline cellulose.

15. The method according to claim 12, wherein the aqueous binder is water or ethanol.

16. The method according to claim 12, wherein the aqueous binder is solution of binder in water or in ethanol.

17. The method according to claim 16, wherein the solution has 0.1 to 80.% (w/v) of concentration.

18. The method according to claim 16, wherein the binder is one or more selected from the group consisting of sucrose, hydroxypropylcellulose, hydroxypropylmethylcellulose, methylcellulose, polyvinylpyrrolidone, pullulan and gum arabic.

19. The method according to claim 12, wherein the spraying powder is not more than 100 μm in particle size.

20. The method according to claim 12, wherein the spraying powder contains 5 to 90% (w/w) of low substituted hydroxypropylcellulose.

21. The method according to claim 12, wherein the spraying powder contains 2 to 70% (w/w) of the drug.

22. The method according to claim 12, wherein the ratio of the aqueous binder to the spraying powder is 1:1 to 1:2.

23. The spherical granules having a core according to claim 1, wherein the spraying powder contains magnesium carbonate and/or calcium carbonate.

24. The spherical granules having a core according to claim 1, wherein the coated spherical granules are further coated with spraying powder containing low substituted hydroxypropylcellulose.

25. The spherical granules having a core according to claim 24, wherein the spherical granules are further coated with an enteric coating agent.

26. The spherical granules having a core 3 according to claim 25, wherein the enteric coating agent is acrylate copolymers anionic in charcter or hydroxypropylmethylcellulose phthalate.

27. The method according to claim 12, wherein the spraying powder contains magnesium carbonate and/or calcium carbonate.

28. The methdo according to claim 12, wherein the spherical granules are further coated with spraying powder containing low substituted hydroxypropylcellulose.

29. The method according to claim 28, wherein the spherical granules are further coated with an enteric coating agent.

30. The methdo according to claim 29, wherein the enteric coating agent is acrylate copolymers anionic in character or hydroxyporpylmethylcellulose phthalate.

* * * * *